United States Patent [19]  
Monties et al.

[11] 4,296,500  
[45] Oct. 27, 1981

[54] ARTIFICAL HEART

[75] Inventors: Jean R. Monties, Auriol; Patrick J. C. Havlik, Marseilles, both of France

[73] Assignee: Agence Nationale de valorisation de la Recherche (ANVAR), France

[21] Appl. No.: 902,364

[22] Filed: May 3, 1978

[30] Foreign Application Priority Data

May 6, 1977 [FR] France .................................. 77 14470

[51] Int. Cl.³ .......................... A61F 1/24; A61M 1/03
[52] U.S. Cl. ....................................... 3/1.7; 128/1 D; 418/54; 418/61 A
[58] Field of Search ............. 3/1.7; 128/1 D, DIG. 3; 418/61 R, 61 A, 61 B, 54

[56] References Cited  
U.S. PATENT DOCUMENTS

| 2,925,814 | 2/1960 | Vibber et al. | 3/1.7 |
| 3,152,340 | 10/1964 | Fry et al. | 3/1.7 |
| 3,221,664 | 12/1965 | Jernaes | 418/61 B |
| 3,387,772 | 6/1968 | Wutz | 418/61 A |
| 3,452,643 | 7/1969 | Pratt | 418/61 A |
| 3,458,120 | 7/1969 | Pfaff et al. | 418/54 |
| 3,533,716 | 10/1970 | Grun | 418/54 |

OTHER PUBLICATIONS

"Pulsatile Flow Blow Pump Based on the Principle of the Wankel Engine" by N. Verbiski et al., Journal of Thoracic & Cardiovascular Surgery, vol. 57, No. 5, May 1969, pp. 753-756.

Primary Examiner—Ronald L. Frinks  
Attorney, Agent, or Firm—Lewis H. Eslinger

[57] ABSTRACT

The present invention relates to an artificial heart which comprises a rotary piston shaped like a trilobar or bilobar hypotrochoid or epitrochoid and a body which defines a cavity which is the rotor casing when the latter is driven both in circular translation of radius e equal to the eccentricity of the trochoid and in rotation about its center with an angular velocity of which the number of revolutions per minute is the same as the pulse of the patient.

10 Claims, 15 Drawing Figures

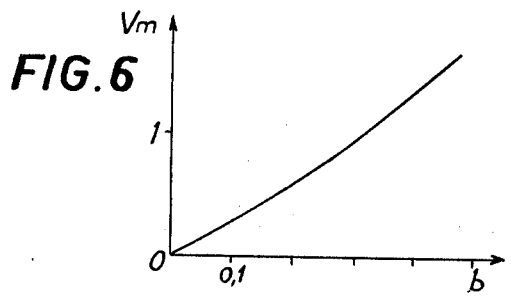
FIG.6
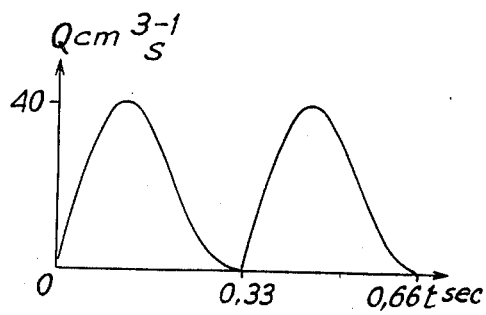
FIG.7
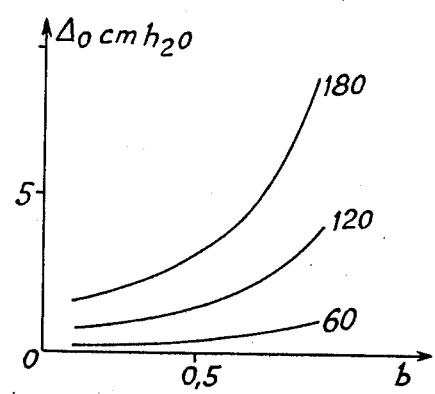
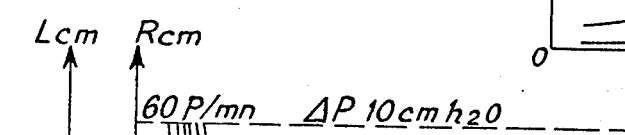
FIG.8
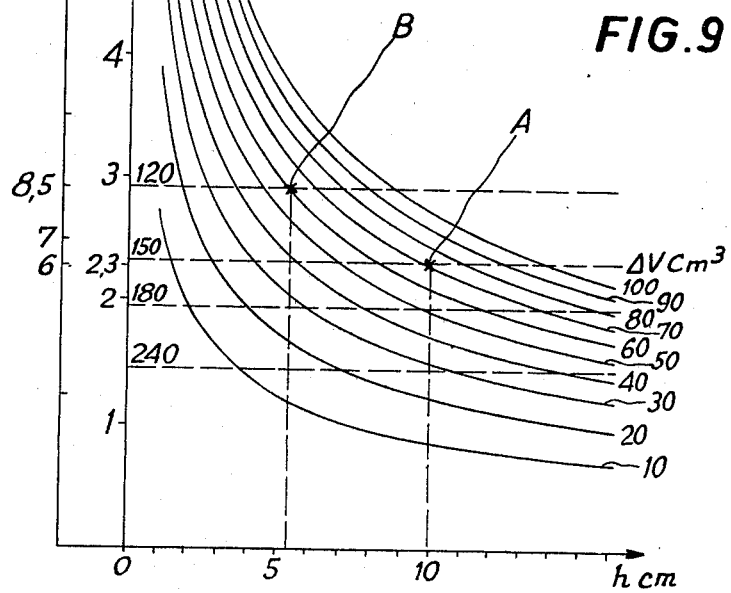
FIG.9

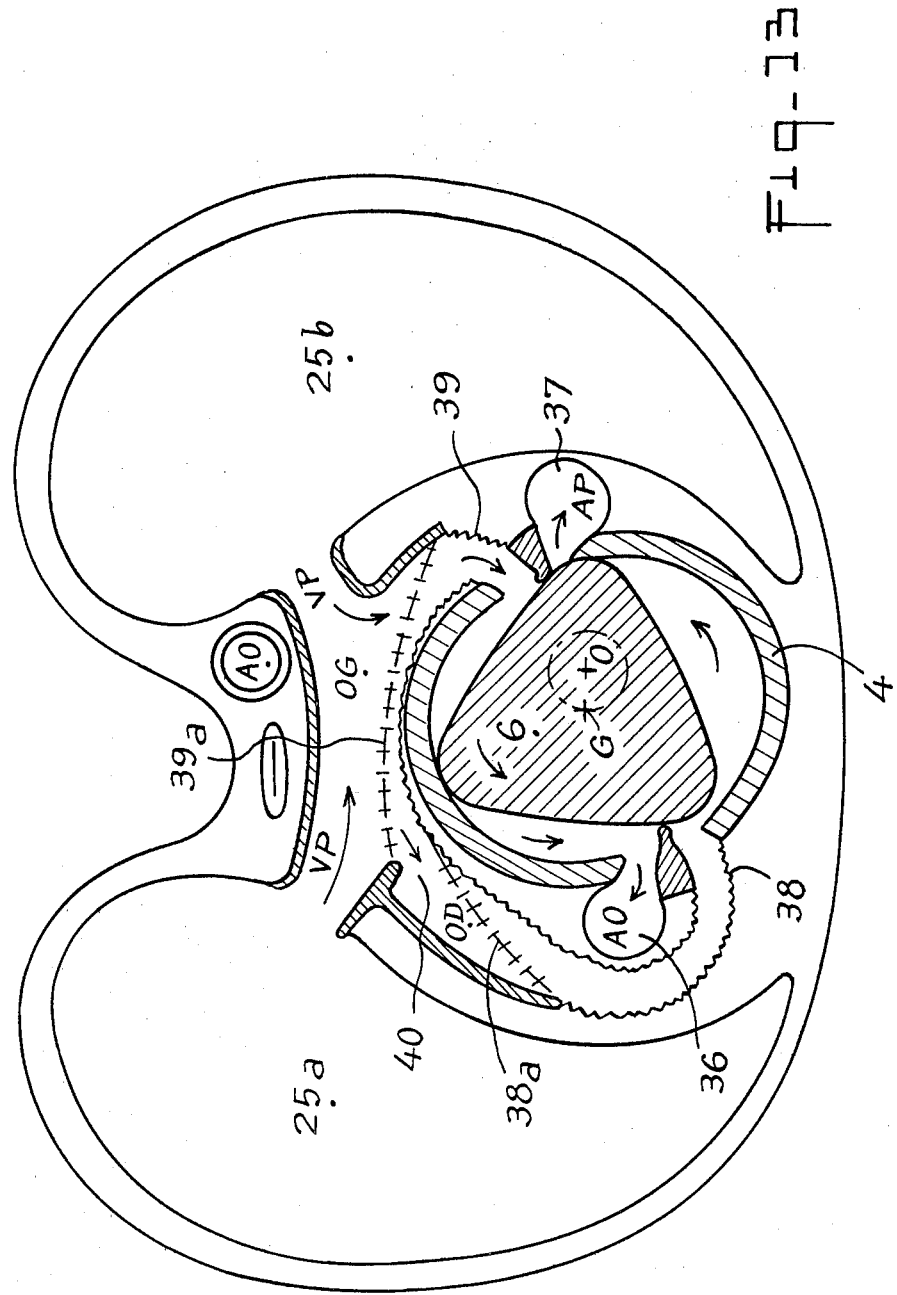

ARTIFICAL HEART

BACKGROUND OF THE INVENTION

The present invention relates to artificial hearts.

Numerous types of artificial hearts have been proposed which serve to assist or completely replace a defective heart.

However, hitherto none of these known artificial hearts has given entire satisfaction through being unable to satisfy the very stringent requirements which must be fulfilled without any possibility of failure.

Reference is made in this connection to the work "Artificial Heart" written by Tetouko Akutsu M.D., Ph.D. and published in 1975 by Igaku Shoin Ltd., Tokyo and by Excerpta Medica, Amsterdam. Reference can also be made to the article "Mechanically Assisted Circulation, the Status of the NHLBI Programme and Recommendations for the Future" which appeared in Volume 1, No. 2 of November 77 of Artificial Organs published by International Society for Artificial Organs, Suite 400 - 10300 Carnegie Avenue, Cleveland, Ohio 44106, U.S.A.

The above two documents contain recent studies of all hitherto known artificial heart types and the conditions which must be fulfilled by these hearts.

A first condition which an implantable artificial heart must satisfy is that its overall dimensions must be sufficiently small to enable it to be implanted and supported by the patient without leading to rejection phenomena and without constituting a too restricting discomfort. This condition will be fulfilled if the dimensions and volumes ejected during each cycle of the artificial heart are of the same order as the dimensions and average systolic ejection volume of the natural heart which varies with age and size between 30 and 100 cc.

A second condition is that the instantaneous flows are pulsatile, i.e. they pass through a maximum during each cycle and are then cancelled out.

A third imperative condition is that the charge loss on aspiration is always below a very low threshold of about 10 cm of water or 10 millibars so as to prevent haemolysis of the blood, whose pressure is reduced. Turbulence which may cause local pressure reductions must be prevented. It is better not to use valves which generate turbulence and whose unsatisfactory operation may have serious consequences.

Obviously another important condition is the complete operational reliability.

Preferably the flow pulsation frequency is the same as the normal pulse and can be easily varied to ensure the regulation of flows as a function of the requirements of the organism. Generally the frequency is regulated in such a way that it maintains an average constant pressure in the aorta.

Such a result can automatically be obtained by a cardiac pump driven by a motor having a constant torque. A pressure rise or fall automatically leads to an increase or decrease in frequency which re-establishes the pressure. Therefore the artificial heart will preferably be driven by a motor having a constant torque.

The documents referred to hereinbefore describe the different types of artificial heart on which experiments have hitherto been performed. None of them comprises a rotary plunger pump of trochoidal, i.e. epitrochoidal or hypotrochoidal shape.

Industrial motors and pumps having a trochoidal rotary plunger are known which are also designated by the name Wankel engines and comprise a cylindrical rotor and a body which defines one or more cylindrical cavities in each of which is placed a rotor, said cavities constituting sleeves or casings of the rotor when the latter is driven both in circular translation and in rotation about its centre.

The following patents describe such motors or pumps: French Pat. 2,250,892 (Gray); French Pat. 2,260,008 (Dornier); French Pat. 2,087,187 (Kaspers); French Pat. 1,166,192 (NSU); U.S. Pat. No. 3,221,664 (Jernaes); German Pat. 2,021,513 (Schultheis); British Pat. 1,350,728 (Dornier).

None of these patents describes the use of a rotary plunger pump of the trochoidal type as a cardiac pump for an artificial heart.

Moreover, the use of these pumps as artificial hearts can also not be gathered from earlier documents describing industrial pumps. A cardiac pump must be rotated at slow speed, i.e. the number of revolutions per minute must correspond to the pulse frequency varying, for example, between 60 and 180 r.p.m., whereas an industrial pump is driven at speeds of 1000 to 3000 r.p.m.

In industrial pumps a sealing defect between the rotor and the stator is partly compensated by the high speed dynamic entrainment of the fluid. In a cardiac pump the sealing between the rotor and the stator must be adequate at low speeds.

The rotor of a trochoidal cardiac pump is driven at uniform speed which is an important advantage for the construction of a drive motor.

To permit its use as a cardiac pump serving to replace the whole heart or half the heart, a trochoidal rotor pump must have two chambers with an admission opening and a discharge opening or four chambers whereof two are provided with an admission opening and two with a discharge opening, whereby said openings must have an adequate passage cross-section so as not to cause too large losses of charge. Moreover, the instantaneous flow from the discharge openings must be pulsatile.

BRIEF SUMMARY OF THE INVENTION

The object of the present invention is to select from the large number of different types of trochoidal rotary piston pumps those which correspond to a complete heart or half-heart model and which best fulfill the numerous requirements made in order to permit them to be used as an artificial heart.

This object is achieved by means of artificial hearts comprising a trochoidal-type rotor which is rotated at uniform speed and whose number of revolutions per minute is equal to the normal pulse rate of the patient in which the trochoid shape is such that the rotor is permanently in substantially tight contact with the inner wall of the body cavity within at least one fixed narrow region parallel to the generating lines and in which the body has on either side of said fixed contact region two elongated openings which are respectively connected to the venous system and to an artery leading to the heart of the patient.

According to a preferred embodiment, a total artificial heart according to the invention comprises a single rotor whose cross-section is a trilobar trochoid and which is permanently in substantially tight contact with the inner wall of the body cavity within two fixed narrow regions parallel to the generating lines and diametrically opposed in such a way that the cavity is separated into two half pumps which are constantly separated from one another by the rotor, whilst the body has four elongated openings arranged pairwise on either side of said fixed regions and namely in the vicinity of the latter, whereby the two openings of the half-pump replacing the right-half heart are connected by pipes respectively to the vena cava and to the pulmonary artery of the patient, whilst the two openings of the other half-pump replacing the left-half heart are connected by corresponding pipes to the pulmonary veins and to the aorta of the patient.

According to the previous embodiment, the cross-section of the rotor is preferably a hypotrochoid with three apices having an eccentricity e and the body defines a cylindrical cavity whose cross-section is the outer casing of the rotor when the latter is driven both in circular translation of radius e and in rotation about its centre in the same direction, with an angular velocity which is three times lower than the angular velocity of the circular translation. The reduced eccentricity $b=e/2R$ of this hypotrochoid is between 0 and 0.5.

Preferably the four openings extend over the entire height h of the body and each of them communicates with a slot of a deformable pipe, said pipes being connected respectively to the pulmonary artery and to the right atrium after ablation of the right ventricle for the openings of one-half pump and to the aorta and the left atrium after ablation of the left ventricle for the openings of the other half-pump.

According to another embodiment, an artificial half-heart has a single rotor whose cross-section is shaped like a bilobar trochoid of eccentricty e, whilst the inner wall of the body cavity is the casing of said rotor when the latter is driven both in circular translation of radius e and in rotation about its centre in the same direction, with an angular velocity two times lower than the angular velocity of circular translation.

In this embodiment the reduced eccentricity $b=e/R$ of the bilobar trochoid is between 0 and 0.33, in such a way that the rotor is permanently in substantially tight contact with the inner wall of the cavity of the body within a fixed narrow region and the body has two elongated openings located on either side of the fixed region and in the vicinity of the latter, said openings being connected respectively by pipes to the vena cava and to the pulmonary artery for the right-half heart and to the pulmonary veins and to the aorta for the left-half heart.

According to a third embodiment, a complete artificial heart comprises two half-hearts according to the preceding embodiment. In this case the body defines two identical cylindrical cavities which are aligned and which are separated from one another by a partition which is perpendicular to the generating lines. It comprises two identical cylindrical rotors mounted on a same drive shaft in rotation and in circular rotation, whereby they are positioned within one of the two cavities.

As a result of the present invention, novel artificial hearts or artificial half-hearts are obtained whose dimensions are of the same order of magnitude as the natural heart and which may be implanted.

One of the advantages of these artificial hearts is that they can be driven in rotation at uniform speed with an implanted electric motor with a constant torque whose construction is known. In this case the blood pressure is automatically regulated.

Another advantage is that the cardiac pumps according to the invention have no valve or any other member with an alternating movement.

Another advantage is that it is possible to machine in series with the requisite high level of precision, which is of the order of one micron, rotors and pump bodies which all have the same cross-section, whereby pumps are obtained which can be adapted to the size and age of each individual patient by varying the height h of the pump.

Therefore the cross-section of the elongated openings varies in proportion to the height h in such a way that the loss of charge remains unchanged.

Another advantage is that complete hearts having a single trilobar rotor with a reduced eccentricity $b=e/2R$ between 0 and 0.5, and which are sub-divided into two half-pumps by the rotor and by the two fixed permanent contact regions of the rotor with the inner wall of the stator cavity represent an analogy with a natural heart. The two half-pumps respectively fulfill the functions of the right half-heart and the left half-heart. Thus, there is a phase displacement equal to $2\alpha/6$ between the discharges of the two delivery chambers but it has been found that such a phase displacement is physiologically admissible.

The embodiment with a rotor shaped like a bilobar trochoid makes it possible to obtain artificial half-hearts which is advantageous in the case of a patient who only requires a prosthesis of a single half-heart.

Moreover it is possible to combine two half-hearts by mounting two identical rotors on the same drive shaft. In this case the discharges of the two half-hearts are completely in phase.

A very important advantage of the pumps according to the invention is that they make it possible to obtain, on the basis of driving in rotation at uniform speed of pulsed flows having a leading edge which is more rapid than the trailing edge, which corresponds to the pulsed flow configuration of a natural heart. This property of certain trochoidal pumps rotating at low speed was neither known nor obvious and justifies the patentability of the use of these pumps as artificial hearts.

The pumps according to the invention can, despite their reduced overall dimensions, discharge during each cycle a volume between 30 and 100 cc which is the requisite volume. It is therefore possible for them to be implanted. However, this application is not limitative and the cardiac pumps according to the invention can also be used as cardiac assistance means which are not implanted or to ensure the circulation of blood during heart surgery.

Another important advantage of the artificial hearts according to the invention is that there is no residual space; all blood which is sucked into the cavity is discharged. Moreove due to the permanent contact between the rotor and the inner wall of the cavity remains within a narrow fixed range or region, it is possible to place the admission and discharge openings directly on either side of this fixed region, thus obtaining relatively wide openings which do not give rise to high losses of charge.

BRIEF DESCRIPTION OF THE DRAWINGS

The invention is described in greater detail hereinafter relative to non-limitative embodiments and with reference to the attached drawings, wherein show:

FIGS. 6, 7, 8 and 9, charts showing the variations in various parameters and the uses of a pump according to FIGS. 3, 4 and 5;

FIGS. 13, 14 and 15, a cross-section and front views from the right and left of a heart according to the invention implanted in the chest.

DETAILED DESCRIPTION OF THE PREFERRED EMBODIMENTS

It is pointed out that trochoids are curves produced by a point of a disc of radius R1 rolling without slipping on the periphery of a fixed circle of radius R2. A distinction is made between epitrochoids which are produced by a point of a disc rolling outside the fixed circle and hypotrochoids which are produced by a point of a disc rolling within a circle. Trochoids are closed curves immediately the ratio n between the radius R2 of the fixed circle and the radius R1 of the movable disc is an integer.

In the case where n=R2/R1=3, epitrochoids or trilobar hypotrochoids with three apices are obtained.

In the case where n=R2/R1=2, epitrochoids or bilobar hypotrochoids of ovoid shape are obtained.

The artificial hearts according to the invention solely comprise trilobar rotors which under certain conditions have two fixed narrow regions of permanent contact between the rotor and the casing and which thus represent a model of a complete heart and bilobar rotors which under certain conditions comprise a fixed narrow region of permanent contact between the rotor and casing and which thus represent a model of a half-heart. By combining two artificial half-hearts whose bilobar rotors are rotated by the same shaft it is possible to obtain a complete artificial heart.

Figure 1:
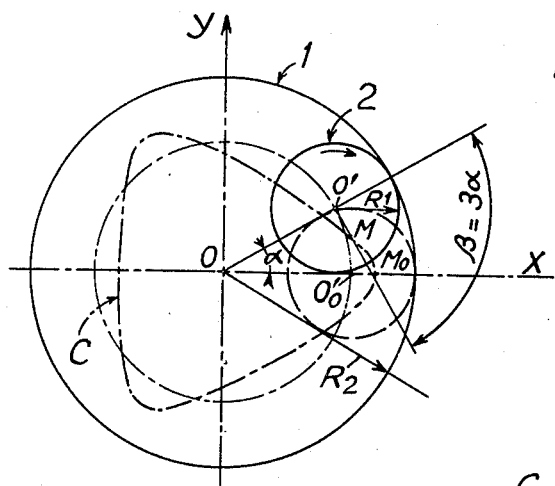
FIGS. 1 and 2, geometrical representations permitting the definition of a hypotrochoid and its envelope.

FIG. 1 permits a geometrical definition of a hypotrochoid with three apices and gives the parametric equation relative to two perpendicular axes OX and OY.

Circle 1 of centre O and radius R2 is a fixed circle. On the inner periphery of the circle rolls without slipping a disc 2 of centre O' and of radius R1=R2/3. The hypotrochoid is curve C produced by a point M of the disc.

It is assumed that O'M=e and R=R2−R1, e being the eccentricity and R the radius of the hypotrochoid. One of the axes of ternary symmetry of the hypotrochoid passing through one of the apices of the latter is selected as the OX axis, this corresponding to the case where the points O, O'o and Mo are aligned, the point Mo then being located outside the segment O, O'o.

In FIG. 1 the initial position of disc 2 is shown by dotted lines and the point which it occupies when the contact point of disc 2 on circle 1 has passed through the angle $\alpha$ is shown in continuous lines. In this second position the radius O'M has turned by an angle $\beta=\beta=3$ due to the equality of the traversed arcs. The vector OM is equal to OO'+O'M.

these two relationships make it possible to give the parametric equations of the coordinates x and y of point M $$x = R[\cos \alpha + b/2 \cos 2\alpha]$$

$$y = R[-\sin \alpha + b/2 \sin 2\alpha]$$

$b=2e/R$ is called the reduced eccentricity.

A cardiac pump according to the invention has a stator whose inner cylindrical surface has a cross-section which is the envelope of the hypotrochoid defined hereinbefore when the centre of gravity of the latter moves along a circle and the hypotrochoid rotates on itself at the same time and in the same direction and at an angular velocity which is three times higher in such a way that when the centre of gravity has performed a complete turn each apex of the hypotrochoid has taken the place of the following apex.

Figure 2:
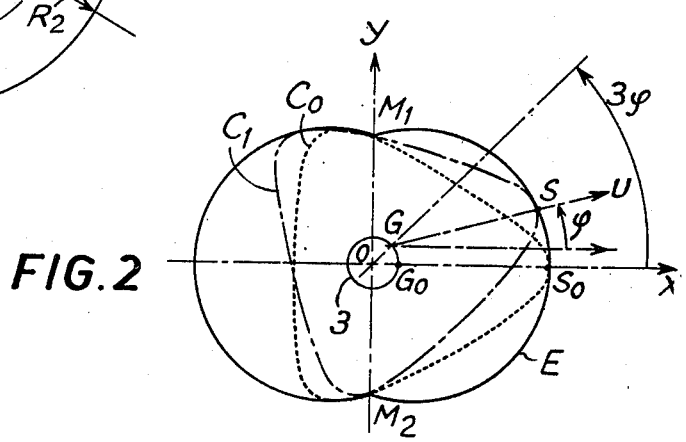

FIG. 2 permits the definition of this envelope and to give its parametric equation relative to axes OX and OY.

The centre of gravity G of the hypotrochoid traverses a circle 3 of centre O and of the radius e and at the same time hypotrochoid C rotates on itself about centre G at an angle velocity which is three times lower and in the same direction.

One of the axes OG passing through an apex So of the hypotrochoid is selected as the OX axis. In FIG. 2 the original position of the hypotrochoid Co of centre Go is shown by dotted lines and the position Cl to which the centre G has turned in counter-clockwise direction by an angle $3\phi$ whilst axis GoSo has reached GS and has turned in the same direction by angle $\phi$ is shown by dot-dash lines.

It is shown that the various positions of the hypotrochoid have an inner and outer double envelope. The generating line of the stator of a pump according to the invention is the outer envelope E.

The parametric equation of the hypotrochoid performing the simultaneous translation and rotation movements is:

$$X = R[\cos(\phi-\alpha) + b/2 \cos(2\alpha+\phi) + b/2 \cos 3\phi]$$

$$Y = R[\sin(\phi-\alpha) + b/2 \sin(2\alpha+\phi) + b/2 \sin 3\phi]$$

The parametric equation of envelope E is:

$$X = R \cos\beta[1 + b[\pm\cos\beta(1-b^2 \sin^2\beta)^{\frac{1}{2}} - b \sin^2\beta]]$$

$$Y = R \sin\beta[1 + b[\pm\cos\beta(1-b^2 \sin^2\beta)^{\frac{1}{2}} + b \cos^2\beta]]$$
with $\beta=\phi-\alpha$.

This equation defines the two envelopes and the outer envelope is chosen as the generating line of the stator. This envelope is close to an epitrochoid but is not one because the same points of the rotor are not always in contact with the envelope.

Calculation of the equation of the envelope makes it possible to establish that the following relationship is satisfied on the envelope:

$\sin(3\phi-2\beta) = b \sin \beta$ which implies that
$0 < b = 2e/R \leq 1$.

The equations of the envelope and the moving hypotrochoid show that there are two points M1 and M2 located on OY at a distance of $O = \pm R$ where the moving hypotrochoid is constantly in contact with the envelope. This property is important. Thus the moving hypotrochoid defines with the envelope two pairs of cavities located on either side of generating lines passing through these two points, which constitute a permanent and fixed separation between these two pairs. In each pair one cavity increases in volume whilst other decreases which has an interesting analogy with the heart which also comprises two separate hearts, a right heart and a left heart each half being separated into two compartments, the atrium and the ventricle.

The above equations show that the greatest width L of the inner cavity of the envelope is located at the intersection of the latter with the OX axis and has a value:

$$L = 2R(1+b).$$

On either side of the fixed points are lateral surfaces which are alternately masked and exposed by the rotor and which thus make it possible to create filling and emptying openings without using valves.

The maximum width of these surfaces measured parallel to the OX axis corresponds to a solution of the equation:

$$\sin(3\phi - 2\beta) \; b \sin \text{ for } \phi = \pi/3$$

giving four points which are symmetrical in pairs relative to the oy axis having for abscissas $$X = \pm R \; b/4(2-b^2).$$

Figure 3:
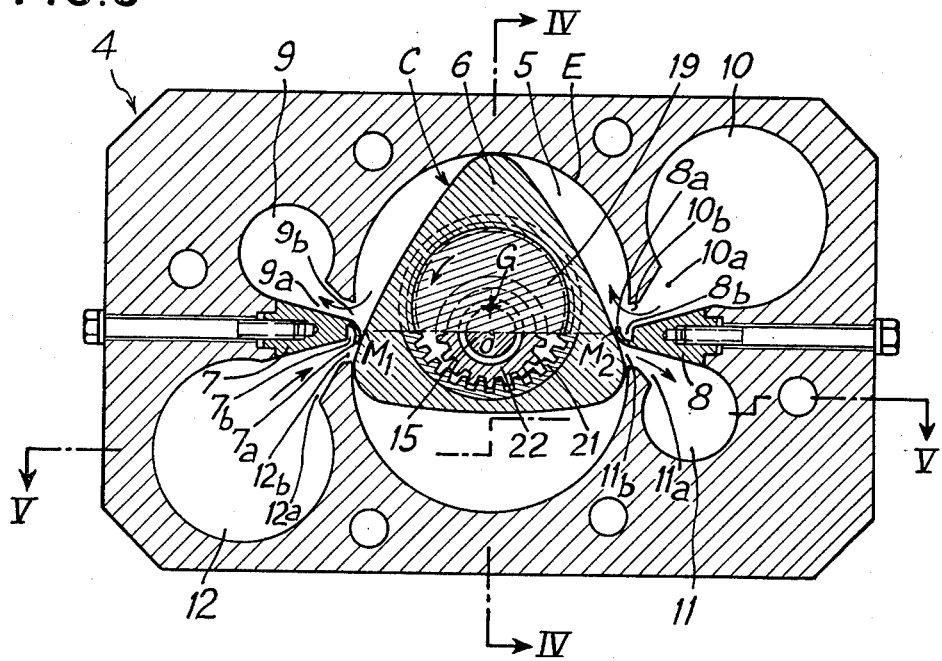
FIGS. 3, 4 and 5, sections of a preferred embodiment of a pump of a complete artificial heart according to the invention.
Figure 4:
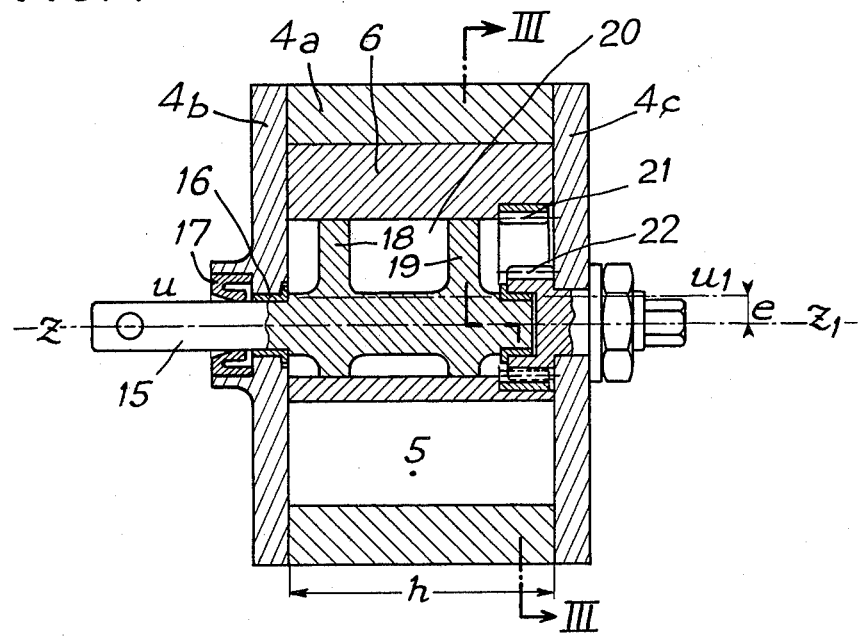
Figure 5:
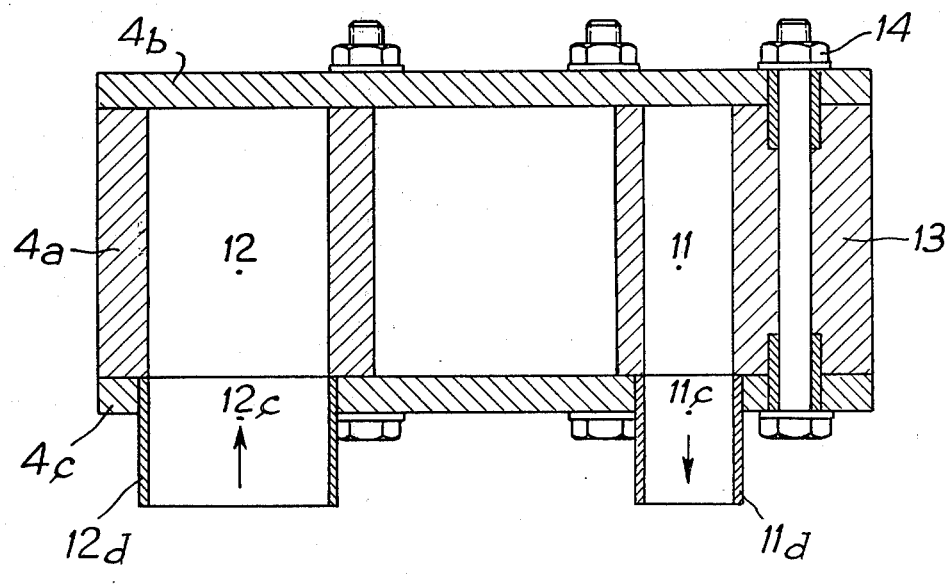

FIGS. 3, 4 and 5 show different sections of a cardiac pump according to the invention comprising a pump body 4 which defines a cavity 5 having a cylindrical volume of height h whose generating lines are supported on a generating curve E which is the hypotrochoid envelope identical to curve E of FIG. 2.

Within the cavity 5 is placed a rotor 6 which has a cylindrical volume of height h whose generating lines are supported on a generating curve C which is a hypotrochoid identical to the hypotrochoid C of FIG. 1 having a centre of gravity G.

The rotor is driven in circular translation about a centre O such that OG=e in such a way that centre G passes through a circle of centre O and of radius e. At the same time rotor 6 is driven in rotation around its centre G in the same direction and at a rotation speed which is three times lower than the rotation speed of centre G. Thus, the movement of rotor 6 reproduces that of the hypotrochoid C of FIG. 2 and the inner surface E of cavity 5 is the rotor casing during this movement.

FIG. 3 shows the fixed points M1 and M2 corresponding to the two generating lines along which the rotor is in permanent contact with the stator.

In each of these two lines the pump body has a member 7, 8 made from an elastomer material and provided with a lip 7a, 8a applied tangentially to the rotor. Between the flexible lips 7a, 8a and members 7, 8 is provided a groove 7b, 8b which permits the reversal of the lips and said grooves are located on the side opposite to the edge on which the rotor engages with the lips.

On either side of generating lines M1 and M2 the pump body has four generally cylindrical channels 9, 10, 11, 12 each of which has a longitudinal slot of height h which is connected by a pipe with a convergent longitudinal profile 9a, 10a, 11a, 12a to an opening 9b, 10b, 11b, 12b. These openings issue into cavity 5 immediately on either side of generating lines M1, M2.

Channels 9 and 11 are discharge channels whilst channels 10 and 12 are admission channels, their volume being larger. Channels 9 and 10 correspond to a half-heart, for example the left half-heart whilst the two channels 11, 12 correspond to the right half-heart.

FIGS. 4 and 5 show in cross-sectional from the structure of the pump body which comprises a central part 4a of width h placed between two lateral flanges 4b, 4c.

Bolts 13 pass through body 4a and the flanges and nuts 14 screw to said bolts to keep body 4a and flanges 4b and 4c tightly assembled.

FIG. 5 shows one of the flanges, for example flange 4c, which has four openings such as 12c and 11c, each of which communicates with one of the channels 9,10,11,12. Each of these openings is provided with a flexible tube end such as 12d, 11d. The tube ends 11d, 12d corresponding to the right half-heart are connected in the case of tube 11d to the pulmonary artery and in the case of tube 12d to the right atrium. In the same way tube end 9d is connected to the aorta whilst tube end 10d is connected to the left atrium.

The maximum width L of openings 9b, 10b, 11b and 12b correspond to the maximum width of the chambers located on either side of points M1 and M2 which, as has been seen, is given by the formula $L = R \; b/4(2-b^2)$. This width consequently passes through a maximum for $b = \sqrt{\frac{2}{3}} = 0.82$.

FIGS. 3 and 4 show the device for driving the pump rotor 6. This comprises a drive shaft 15 of axis z z1 passing through point O of FIG. 3. The shaft is rotated by a variable speed motor which is not shown.

The speed variation of the motor makes it possible to vary the pulse and regulate the blood flow rate as a function of the requirements of the organism.

Shaft 15 passes through flange 4b and is supported by a friction-preventing ring 16, whilst a lip joint 17 ensures the sealing of the passage.

Shaft 15 carries two off-centre circular cams 18,19 whose centre is located on an axis u u1 parallel to the axis z z1 and spaced from the latter by a length e. A central bore 20 of centre G having the same external diameter as cams 18,19 passes through rotor 6 and the cam shaft 15 is engaged within the said bore with a limited tolerance. When shaft 15 is rotated the centre of gravity G of the rotor is driven in circular translation along a circle of centre O and radius e.

The rotor bears against stator E and normally the reaction of the stator is sufficient to force the rotor to pivot about centre G with a rotation speed which is three times less than the angular velocity of displacement of centre G on its circular trajectory. However, in order to facilitate the rotation of the rotor about its centre and decrease friction with the inner wall of the stator, it is preferable to force the rotor to rotate.

To this end the rotor has at one of its ends a crown gear 21 placed on the inner periphery of bore 20. In addition a fixed toothed pinion 22 coaxial to the shaft is mounted on the body. The ratio between the radii of the crown gear 21 and pinion 22 is equal to 3/2 in such a way that the crown gear 21 rolls without slipping on the pinion and rotates about its centre with an angular velocity equal to one-third of the angular velocity of the shaft.

FIG. 3 is a section of FIG. 4 along the broken line III—III which in the upper half of the section passes through cam 19 and in the lower half through a crown gear 21 and pinion 22.

The radius r of bore 20 and cams 18 and 19 must be less than the radius of the circle in the hypotrochoid $r \leq R - e \leq R(1-b/2)$. The eccentricity e of cams 18,19 must necessarily be less than r, so that: $e = Rb/2 < R(1-b/2)$ and therefore $b < 1$.

In the case where a crown gear and a fixed pinion having radii in the ratio 3/2 are used to control the rotational movement of the rotor, it can be shown that b must be less than 0.5. In practice b is chosen as close to 0.4.

FIG. 6 is a chart which gives the variation as a function of b plotted on the abscissa, of the volume vm discharged for each pulsation for a pump whose radius R and height h are equal to 1. To obtain the discharged volume it is merely necessary to read off this chart the value of vm corresponding to the value of b and multiply vm by $R^2$ and by h. Thus, for $b=0.4$, vm is close to 1.33 and the volume discharged per pulsation is substantially equal to $1.33.R^2.h.cc$.

The discharged volume increases in proportion to h as does the passage cross-section of the openings. Thus, a constant radius R can be chosen which facilitates the machining of the rotor and stator and it is then merely necessary to vary width h to adapt the cardiac pump to a particular patient because it is known that the volume necessary per pulsation varies between 30 and 100 cc depending on the age and size of individual persons. Ths loss of charge on passing through the openings remains constant.

FIG. 7 represents the flow variations Q measured in $Cm^3.s^{-1}$ as a function of time for a rotation speed of the rotor on itself of 60 r.p.m., i.e. 180 pulsations per minute, for a thickness of unity, a radius $R=2$ cm and a reduced eccentricity $b=\frac{1}{2}$. This curve shows the pulsatile course of the instantaneous flow and shows that the selection of a cardiac pump according to the invention makes it possible to meet an essential physiological requirement, namely that of obtaining a pulsatile flow rate identical to that produced by the normal heart.

A very important factor of a cardiac pump is the loss of charge through the admission openings because it is imperative that the maximum pressure reduction in the admission chambers does not drop below a threshold which is approximately 10 millibars, because beyond this threshold the blood is destroyed by haemolysis.

FIG. 8 shows the variations in the pressure reduction on suction $\Delta o$ measured in cm of water as a function of the eccentricity b for a radius of unity. For a given radius R the pressure reduction $\Delta p$ is equal to $\Delta o.R^2$.

FIG. 8 gives the development of the pressure reductions on suction for three pulsation frequencies 60, 120 and 180, the pressure reduction $\Delta o$ varying like the square of the frequency.

The physiological and technical constraints placed on a cardiac pump according to the invention are as follows.

The driving of the rotor by a corwn gear and a fixed toothed pinion having radii in the ratio 3/2 drives $b < 0.5$.

As the toothing of the gears cannot drop below certain limits an eccentricity of $b=0.4$ is chosen which leads to a pump located within a cylinder of height h and diameter $L=2.8$ R. The dimensions must remain small to permit implantation in the chest. The rotation speed which determines the frequency of the pulsations must be in accordance with the pulse of the person or animal receiving the pump ad as the flow is regulated by a frequency variation it is necessary to provide a maximum frequency which is three times the basic frequency.

The systolic discharge volume $\Delta V$ is dependent on the age and weight of the person. It may vary between 30 and 100 cc depending on individuals. It is dependent on the height h and radius R in accordance with the relationship $\Delta V = 1.33.h.R^2$.

The maximum pressure reduction permitted on filling $\Delta p$ must remain below 10 cm of water. If it is necessary to vary the height h, $\Delta p$ must not vary. However, $\Delta p$ is dependent on the frequency N and the radius R in accordance with a relationship of form $\Delta p = K.N^2.R^2$.

This formula shows that in order to respect a maximum $\Delta p$, when frequency N increases, R decreases very rapidly.

FIG. 9 is a chart showing on the abscissa the values of height h and on the ordinate the values of radius R and the maximum width L measured in cm.

Curves indicating the variations of L and R as a function of h are plotted for different systolic flow rates $\Delta V$ varying between 10 and 100 cc.

Horizontal dotted lines indicate the upper maximum limits corresponding to a pressure reduction $\Delta p = 10$ cm of water for various pulsation frequencies varying between 60 and 240 pulsations/minute.

As a numerical non-limitative example, on selecting $b=0.4$ a systolic volume $\Delta V=70$ cc and a height $h=10$ cm, the chart of FIG. 9 shows that for a maximum pulsation frequency below 150, it is possible to select a point of chart A corresponding to a pump with a radius $R=23$ mm and a widthwise dimension $L=60$ mm. Flow rate and pulsation frequency values are obtained which are compatible with the blood circulation of man by means of a pump whose dimensions are similar to those of a heart.

It is also possible to select a slightly larger radius R, for example $R=30$ mm, whilst maintaining $b=0.4$. In this case the position assumed is for example point B which corresponds to $\Delta V=60$ cc $h=55$ mm and $L=85$ mm. A more compact pump is obtained but the pulsation frequency cannot exceed 120 pulsations per minute.

The charts show that by constructing rotors having a radius R between 20 and 35 mm and a total width L between 45 and 100 mm, it is possible in the least favourable case to reach pulsation frequencies of approximately 100 to 180 pulsations per minute and to vary the systolic discharge rate between 30 and 100 cc by varying height h between 50 and 150 mm which makes it possible to cover most of the cases encountered in practice, whilst adhering to the dimensions which permit an implant.

Calculations show that the power necessary for driving a pump according to the invention is approximately 3.5 W and the energy consumed is approximately 1.2 joule per pulsation.

Figures 10, 11, 12:
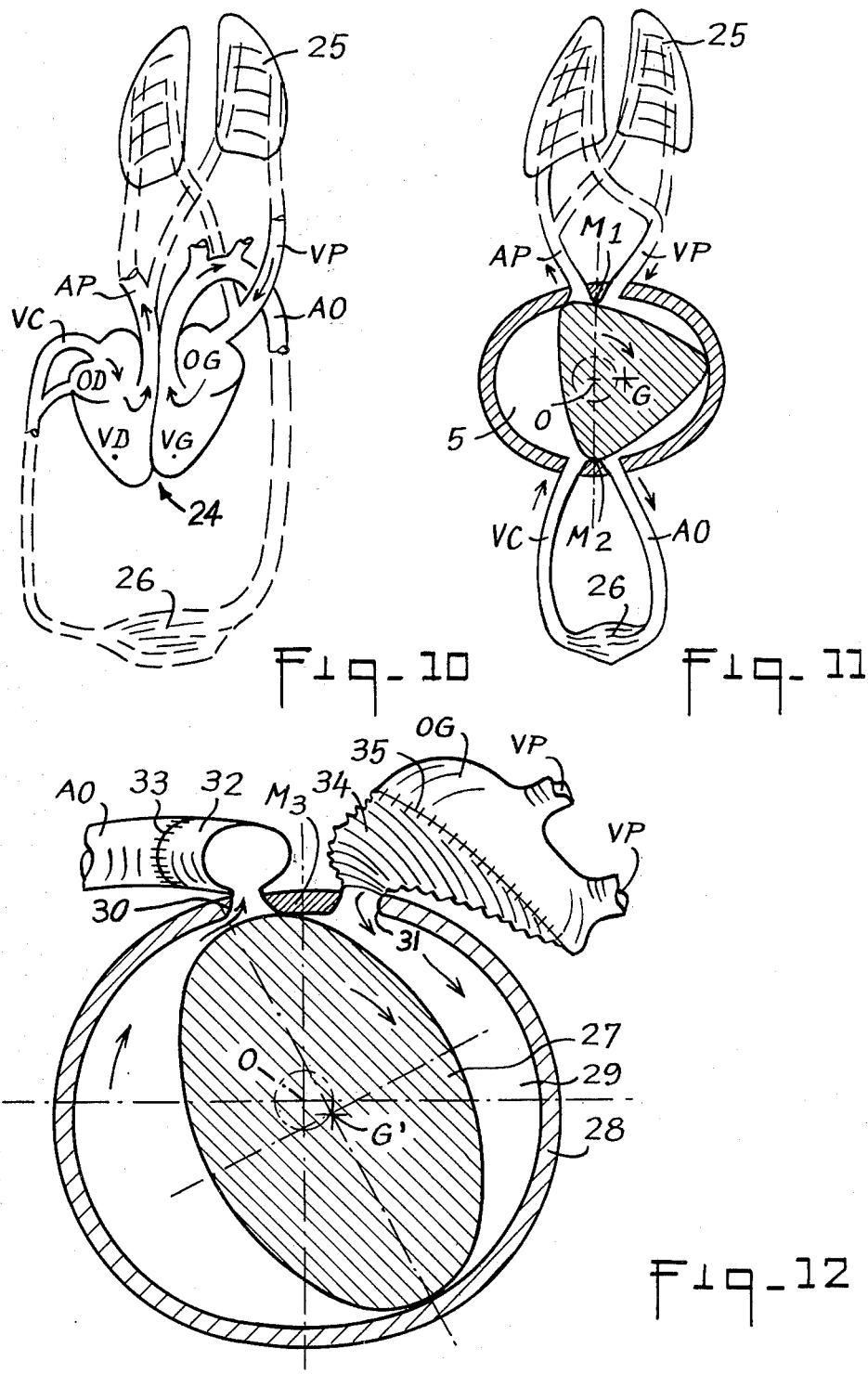
FIGS. 10 and 11, two general diagrams showing the blood circulation with a natural heart and with a total artificial heart according to the invention.
FIG. 12, an embodiment of an artificial half-heart according to the invention.

FIG. 10 is a general diagram showing the blood circulation indicating the human heart viewed from the front with the right atrium (OD) to which lead the vena cava (VC), the right ventricle (VD) from which issues the pulmonary artery (AP), the left atrium (OG) which receives the pulmonary veins (VP) and the left ventricle (VG) from which issues the aorta (AO). Reference numeral 24 designates the heart, 25 the lungs and 26 the capillaries.

The similar diagram of FIG. 11 shows the interconnections of a complete artificial heart according to FIGS. 3 to 5 with the blood vessels. It can be seen that cavity 5 is sub-divided into two halves which are constantly separated from one another by the rotor which is in permanent contact with the body along two fixed regions M1 and M2 which are diametrically opposite. The half-pump located to the left of the separating line M1,M2 has two openings, namely an admission opening which is connected to the vena cava VC and a discharge opening which is connected to the pulmonary artery. This half-pump replaces the right half-heart. The other half-pump located to the right of the separating line M1,M2 has an admission opening which is connected to the pulmonary veins VP and a discharge opening which is connected to the aorta AO, said half-pump replacing the left half-heart.

A total artificial heart having a rotor in the form of a trilobar hypotrochoid has been described. It is pointed out that in the case of a rotor in the form of a trilobar epitrochoid, which is the case with the Wankel engine, if the reduced eccentricity $b=2e/R$ is between 0 and 0.5 the rotor still remains in permanent contact with two narrow fixed regions of the stator which serve the same function as the two lines M1 and M2 and it is also possible to construct a complete artificial heart which is connected to the blood vessels according to the diagram of FIG. 11 and which has a rotor in the form of a trilobar epitrochoid having a reduced eccentricity b between 0 and 0.5.

FIG. 12 shows another embodiment of an artificial half-heart. In this case the cylindrical rotor 27 of centre G' has a cross-section in the form of a bilobar trochoid, for example a bilobar hypotrochoid in the case of the drawing.

Returning to the geometrical drawing FIG. 1, it is pointed out that a bilobar hypotrochoid is the closed curve traversed by a point M of disc 2 of radius R1 which rolls within the fixed circle 1 of radius R2 when $R2/R1=2$. The distance $O'M=3$ and $R2-R1=R1$.

The parametric equations relative to axes OX and OY are then:

$X=R1+e) \cos a$ $Y=R1+e) \sin a$

The body of pump 28 defines a cylindrical cavity 29 whose cross-section is the outer casing of rotor 27 when the latter is driven both in circular translation of radius e and in rotation about its centre G' with an angular velocity of the same direction as the circular translation speed and which is equal to half the latter.

If the reduced eccentricity $b=e/R1$ is between 0 and 0.33, the rotor remains in permanent contact with a fixed narrow region of body M3 which can be lined with an elastic material in order to improve sealing.

Body 28 is provided with two elongated openings 30,31 which are disposed on either side of region M3 and which extend over the entire height h of body 28. Opening 30, which is the discharge opening, is connected to a slot of a cylindrical pipe 32 which is connected by a circular stitching 33, for example to the aorta OA in the case of a left half-heart or the the pulmonary artery in the case of a right half-heart.

Opening 31 which is the admission opening is connected via a deformable pipe 34, for example a pipe having undulations in the form of a bellows and which is connected by peripheral stitching 35 to a left atrium (OG) (FIG. 12) or to the right atrium (in the case of the right half-heart) following the ablation of the corresponding ventricle.

The latter embodiment is preferred in the case where it is desired to effect a prosthesis of only one half-heart. It is also possible to obtain a complete artificial heart by combining two artificial half-hearts; such is the case in FIG. 12. In this case body 28 has two identical cylindrical cavities which are aligned and separated from one another by a transverse partition. Each of the cavities contains an identical bilobar rotor and the two rotors are mounted on the same drive shaft in rotation and in circular translation. Each cavity has two openings, namely an admission opening and a discharge opening and replaces one half-heart and two half-hearts operating in synchronism and in phase.

Figure 15:
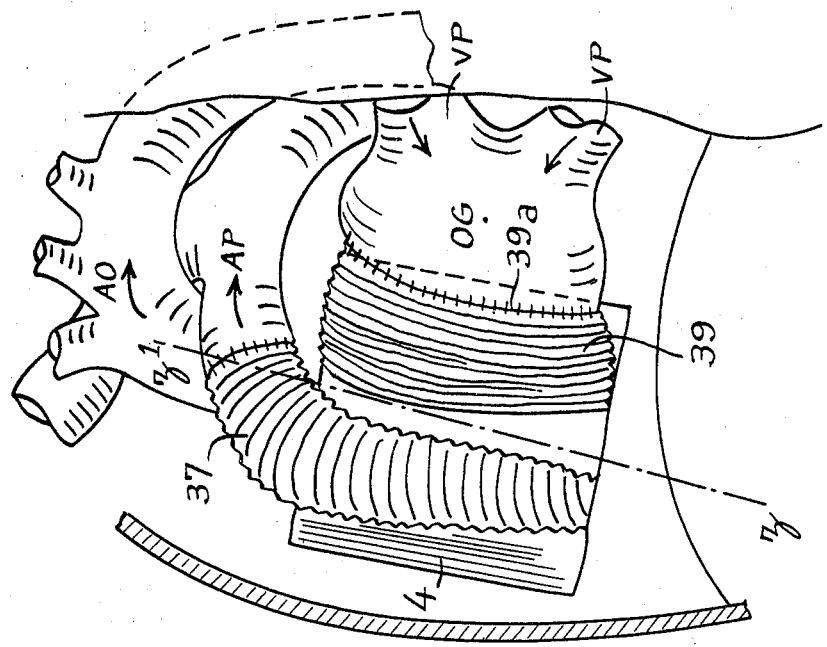
Figure 14:
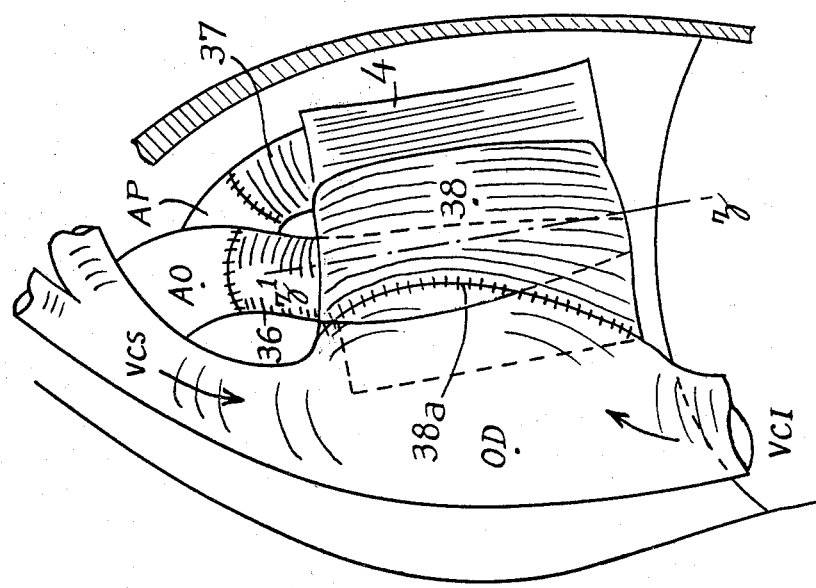

FIGS. 13, 14 and 15 show a complete artificial heart according to the invention implanted in the chest of a patient. The rotation axis z z1 of the rotor which is parallel to the generating line of the rotor and the body is substantially vertical. Due to this arrangement the available heightwise space varies in the same sense as the size of the person and also varies in the same sense as the height h of the artificial heart.

The artificial heart implant takes place in accordance with known surgical methods according to which the two ventricles undergo ablation and the two admission openings of the artificial heart are connected to the artria.

FIG. 13 shows the pump body 4 and the rotor 6. The two discharge openings are connected to circular pipes 36,37 which are themselves respectively connected to the aorta AO and the pulmonary artery AP. The two admission openings are connected by deformable pipes 38,39 respectively to the right atrium by a peripheral stitching 38a and to the left atrium by a peripheral stitching 39a. An opening 40 links the two pipes 38,39 and this opening serves to establish a shunt flow from the left atrium to the right atrium in order to re-establish the flow balance.

FIG. 14 is a view from the left in which it is possible to see the right atrium OD which receives the upper vena cava VCS and the lower vena cava VCI which is connected by stitching 38a to a deformable pipe 38. It is also possible to see the aorta AO which is connected to pipe 36 and the pulmonary artery AP which is connected to pipe 37.

FIG. 15 is a view from the right in which it is possible to see the artificial heart 4, the left atrium OG which receives the pulmonary veins VP and which is sewn by peripheral stitching 39a to the deformable pipe 39 which connects it to an admission opening of the pump. The adjacent opening which is a discharge opening is connected by deformable pipe 37 to the pulmonary artery AP.

The invention is not limited to the embodiments described and represented hereinbefore and various modifications can be made thereto without passing beyond the scope of the invention.

What is claimed is:

1. An artifical heart comprising a cylindrical rotor and a body which defines a cylindrical cavity, the cross-sections of said rotor and said cavity being respectively a trochoid and the envelope of said trochoid when the rotor is driven both in circular translation and in rotation about its centre, means for driving the rotor in rotation at a uniform speed, the number of revolutions per minute of which is the same as the ormal pulse rate of the patient, whereby the body has at least one fixed narrow region parallel to the generating lines within which the rotor is permanently in substantially tight contact with the inner wall of the cavity, said body having two elongated openings located on either side of the fixed region which are adapted to be connected respectively to the venous system and to an artery leading to the heart of the patient.

2. A complete artificial heart comprising a single cylindrical rotor and a body which defines a cylindrical cavity within which is located the said rotor, wherein the cross-section of the rotor is shaped like a trilobar trochoid and the said cylindrical cavity is the envelope of the rotor when the latter is driven both in circular translation and in rotation, means for driving the rotor in rotation at a uniform speed at which the number of revolutions per minute is the same as the normal pulse rate of the patient, whereby said body has two fixed narrow regions parallel to the generating lines of the body within which the rotor is permanently in substantially tight contact with the inner wall of the cavity, said regions being diametrically opposite and sub-dividing the cavity into first and second half-pumps separated from one another by the rotor, said body having four elongated openings arranged on either side of the fixed regions and in the vicinity of the latter, the two openings of the first half pump are respectively adapted to be connected to the vena cava and pulmonary artery of the patient to replace the right half-heart of the patient and the two openings of the second half-pump are adapted to be connected respectively to the pulmonary veins and to the aorta of the patient to replace the left half-heart of the patient.

3. A complete artificial heart according to claim 2, wherein the cross-section of the trilobar rotor is a hypotrochoid with three apices having an eccentricity e, said body defining a cylindrical cavity whose cross-section is the outer casing of the rotor when the latter is driven both in circular translation of radius e and in rotation about its centre in the same direction with an angular velocity which is three times lower than the angular velocity of the circular translation.

4. A complete artificial heart according to claim 3, wherein the reduced eccentricity $b=2e/R$ of the said hypotrochoid is between 0 and 0.5.

5. A complete artificial heart according to claim 2, wherein the elongated openings extend over the entire length of the body and each of them communicates with a slot in a pipe, said pipes being adapted to be connected respectively to the right atrium and to the pulmonary artery in the case of the first half-pump and to the left atrium and to the aorta in the case of the second half-pump.

6. A complete artificial heart according to claim 5 wherein the two pipes are adapted to be respectively connected to the aorta and to the pulmonary artery and have a cross-section which is less than that of the pipes connected to the atria.

7. A complete artificial heart according to claim 2 wherein the pump body has two lip joints which are diametrically opposite and located along the two fixed regions at which the rotor is in permanent contact with the inner wall of the cavity.

8. A complete artificial heart which can be implanted in a human being according to claim 2, wherein the hypotrochoid forming the rotor has a radius R between 20 and 35 mm and a height h parallel to the rotational drive axis which varies according to the particular person between 50 and 150 mm, making it possible to obtain systolic discharge volumes between 30 and 100 cc.

9. An artificial half-heart comprising a cylindrical rotor and a body which defines a cylindrical cavity within which is located the rotor wherein the cross-section of the rotor has the shape of a bilobar trochoid and the inner wall of the cylindrical cavity is the casing of the said rotor when the latter is driven both in circular translation of radius e and in rotation about its centre, in the same direction and at an angular velocity which is two times lower than the angular velocity of circular trnaslation, means for rotating the rotor at a slow uniform speed of which the number of revolutions per minute is the same as the pulse rate of the patient, and the reduced eccentricity $b=e/R1$ of said bilobar trochoid is between 0 and 0.33 whereby the body has a narrow region which is parallel to the generating lines and within which the rotor is in permanent and substantially tightly sealed contact with the inner wall of the body and in which the body has two elongated openings located on either side of said region, and deformable pipes respectively adapted to connect said openings to the vena cava and to the pulmonary artery when the said artificial half-heart replaces a right halfheart or to the pulmonary veins and aorta when said half-heart replaces a left half-heart.

10. A complete artificial heart comprising a body which defines two cylindrical cavities which are aligned and separated from one another by a partition perpendicular to the generating lines and two identical cylindrical rotors mounted on the same drive shaft and each located within one of the said cavities, wherein the cross-section of the rotors has the form of a bilobar trochoid of eccentricity e and the inner wall of the said cylindrical cavities is the casing of a rotor when the latter is driven both in circular translation of radius e and in rotation about its centre in the same direction with an angular velocity which is two times lower than the angular velocity of circular translation, means for driving said rotor in rotation at a slow uniform speed of which the number of revolutions per minute is equal to the pulse rate of the patient and the reduced eccentricity $b=e/R1$ of said rotors is between 0 and 0.33 in such a way that the said body has a narrow range parallel to the generating lines within which each of the rotors is in permanent and substantially tightly sealed contact with the said inner wall and in which each of the said cavities has two elongated openings on either side of the fixed region, and deformable pipes adapted to respectively connect said openings to the vena cava and pulmonary artery for openings of a cavity replacing the right half-heart and to the aorta and pulmonary veins for openings of the other cavity replacing the left half-heart.

* * * * *